United States Patent [19]

Crow et al.

[11] Patent Number: 5,662,647

[45] Date of Patent: Sep. 2, 1997

[54] ELECTRODE ASSEMBLY FOR ELECTROSURGICAL INSTRUMENT

[75] Inventors: Lowell Crow, Danville; Allen R. Howes, San Ramon, both of Calif.

[73] Assignee: Transamerican Technologies International, Pleasanton, Calif.

[21] Appl. No.: 406,035

[22] Filed: Mar. 17, 1995

Related U.S. Application Data

[63] Continuation-in-part of Ser. No. 207,245, Mar. 7, 1994, abandoned, which is a continuation of Ser. No. 724,689, Jul. 22, 1991, abandoned.

[51] Int. Cl.⁶ .................................................. A61B 17/36
[52] U.S. Cl. .................... 606/41; 606/46; 606/49
[58] Field of Search ............................ 606/32-52

[56] References Cited

U.S. PATENT DOCUMENTS

| | | | |
|---|---|---|---|
| 1,813,902 | 7/1931 | Bovie | 606/42 |
| 1,952,617 | 3/1934 | Wappler . | |
| 2,448,741 | 9/1948 | Scott et al. . | |
| 3,799,168 | 3/1974 | Peters . | |
| 3,805,791 | 4/1974 | Seuberth et al. . | |
| 3,835,842 | 9/1974 | Iglesias | 606/46 |
| 4,294,254 | 10/1981 | Chamness | 606/47 |
| 4,445,892 | 5/1984 | Hussein et al. . | |
| 4,485,812 | 12/1984 | Harada et al. . | |
| 4,506,668 | 3/1985 | König | 606/46 |
| 4,657,018 | 4/1987 | Happy | 606/46 |
| 4,919,129 | 4/1990 | Weber, Jr. et al. . | |
| 5,088,998 | 2/1992 | Sakashita et al. | 606/40 |
| 5,195,958 | 3/1993 | Phillips | 606/40 |
| 5,348,555 | 9/1994 | Zinnanti | 606/49 |
| 5,449,356 | 9/1995 | Walbrink | 606/40 |
| 5,449,357 | 9/1995 | Zinnanti | 606/49 |

FOREIGN PATENT DOCUMENTS

| | | | |
|---|---|---|---|
| 189 329 A | 7/1986 | European Pat. Off. . | |
| 2265 344 | 11/1975 | France . | |
| 365912 | 12/1922 | Germany | 604/51 |

OTHER PUBLICATIONS

© Wiltek Medical, Inc. 1991, identifies probe models under catalog nos. LEP-37010, 37030, and 37040, 1991.
Ximed surgical Accessories Price List, p. 6, Ximed Medical Systems, Santa Clara, California 95050.
Olinger et al., "Eighteen-Gauge Microscopic-Telescopic Needle Endoscope with Electrode Channel . . . ", *Surg. Neurol.* 1974, 2:151–159.
*American Heritage Dictionary*, pp. 234 and 248.

*Primary Examiner*—David M. Shay
*Attorney, Agent, or Firm*—Townsend and Townsend and Crew LLP

[57] ABSTRACT

An electrosurgical system includes an electrode assembly which is detachably combined with an aspiration/irrigation cannula. The electrode assembly includes a shaft having an electrode tip at its distal end and a connector plug at its proximal end. A sleeve slidably and rotatably received on the proximal end of the shaft includes connecting means for securing to a proximal housing on the cannula. The system includes both the cannula and electrode assembly and is useful in performing electrosurgical procedures as part of minimally invasive surgical operations. A non-conductive cannula and valve housing are also provided which prevent capacitive coupling between the cannula and a monopole electrode.

21 Claims, 5 Drawing Sheets

ELECTRODE ASSEMBLY FOR ELECTROSURGICAL INSTRUMENT

BACKGROUND OF THE INVENTION

This application is a continuation-in-part of U.S. patent application Ser. No. 08/207,245 filed Mar. 7, 1994, which in turn, was a continuation of U.S. patent application Ser. No. 07/724,689, filed Jul. 2, 1991, both now abandoned.

FIELD OF THE INVENTION

The present invention relates generally to the structure and use of surgical instruments. More particularly, the present invention relates to the structure and use of an electrode assembly in combination with a cannula in surgical procedures.

Electrosurgery refers generally to medical treatment procedures which apply electrical energy to tissue or body organs to effect a desired change, such as cauterization, cutting, and the like. Usually, a high frequency electrical current is applied to the body tissues to cause severing and/or seal small blood vessels by electrocauterization.

Of particular interest to the present invention are monopolar electrosurgical devices, where the patient is grounded and a very high frequency electrical current is applied to a treatment site using a specialized electrode. In general, electrosurgical procedures are desirable since they reduce bleeding from small blood vessels, which in turn facilitates the handling of highly vascular tissues while minimizing exposure of the patient to shock and pain.

An expanding field of surgery referred to generally as endoscopy and including laparoscopic, endoscopic, and arthroscopic surgery, relies on "minimally invasive surgical" (MIS) techniques where specialized instruments are introduced through narrow diameter tubes, such as trocar sleeves, while the treating physician observes manipulation of the instruments through specialized imaging equipment (endoscopes), such as laparoscopes and arthroscopes enhanced by video technology. Such MIS surgical techniques offer significant advantages over conventional "surgical procedures". In particular, the MIS techniques are usually less traumatic, require shorter recovery time, and are less costly than corresponding conventional surgical techniques.

The use of electrosurgical devices and methods in MIS surgical procedures is well known. Usually, a narrow diameter electrosurgical probe is introduced through a previously placed trocar sleeve and is used to perform cauterization or severing of tissue, or the like, while the physician observes the procedure on the imaging equipment. Thus, the benefits of both electrosurgery and MIS can be combined to the great benefit of the patient.

The use of electrosurgical instruments in MIS procedures, however, can be problematic. In particular, the incorporation of only a single type of electrode with a limited function necessitates frequent exchange and replacement of the instrument through the trocar sleeve. Additionally, electrosurgical procedures frequently create smoke near the treatment site, obscuring the treating physician's view of the treatment site through the imaging equipment.

These problems have been at least partly addressed by the design of electrocautery probes having a single irrigation (or aspiration) port and a retractable electrode. Such electrocautery probes are commercially available from Wiltek Medical, Inc., Winston-Salem, N.C. 27116. While an improvement over previous electrocautery devices, the Wiltek electrocautery probes do not permit replacement of the internal electrode assembly within the outer irrigation/aspiration tube. Thus, the entire assembly of the electrode and irrigation/aspiration tube must be removed and replaced whenever a different type of electrode is required. In addition to being inconvenient, the need to replace the entire integrated assembly is costly and requires that a full set of all electrode types be available. Moreover, the Wiltek electrocautery probes include only a single irrigation or aspiration port. Thus, these devices require the user to replace the connecting tube on the port whenever it is desired to switch from aspiration to irrigation, or vice versa or to utilize a two-way stopcock or similar device.

A second type of electrosurgical probe is available from Ximed Medical Systems, Santa Clara, Calif. 94505. The electrosurgical probe also combines an irrigation/aspiration tube with an internal electrode element. While the Ximed probe does include separate aspiration and irrigation valves, it does not permit retraction or rotation of the electrode relative to the aspiration tube. Thus, manipulation of the electrode can be problematic (since the proximal end of the tube is connected to both irrigation and aspiration tubes).

Additionally, prior art electrosurgical instruments have been found to be susceptible to capacitive coupling. Capacitive coupling is a largely unrecognized phenomenon which can produce significant deleterious effects during electrosurgery. As described above, monopolar electrosurgery typically includes the introduction of a narrow electrosurgical probe through a sleeve positioned in a grounded patient body. The probe is electrically isolated from the sleeve in part to prevent the inadvertent application of electrical energy through the sleeve to organs and tissues. However, the sleeves used in prior art electrosurgical systems comprise metallic structures, typically a high strength biocompatible alloy such as stainless steel. Such metallic sleeves have recently been found to form capacitors when disposed around the electrode, thereby creating an electrical potential in the sleeve. Clinically, this effect, herein referred to as capacitive coupling, has been found to lead to serious complications when the electrical potential from a conductive sleeve discharges as an induced current to an internal organ such as a bowel.

Furthermore, the electrosurgical systems of the prior art have often been difficult or impossible to sterilize. The increasing importance of cost efficiency in the medical field in recent years has made it increasingly desirable to re-use surgical equipment. Preferably, surgical equipment is steam cleaned in autoclaves. However, prior art electrosurgical assemblies have included insulations and other materials which will not withstand repeated high temperature sterilization. Additionally, the complexity of many prior art systems make cleaning and sterilization extremely time consuming and costly.

For these reasons, it would be desirable to provide improved electrosurgical probe designs for use in MIS procedures. In particular, it would be desirable to provide electrosurgical instruments which incorporate both an electrode assembly and a tube for providing aspiration and irrigation of the area being treated. It would be further desirable to provide an electrode assembly which can be detachably mounted within a conventional aspiration/irrigation cannula so that the need to provide a full range of integrated devices is overcome. The electrode assemblies should also permit both rotation and axial retraction of the electrode relative to the cannula in which it is been mounted. The electrode assembly should still further provide a seal to prevent leakage of fluid through the assembly during use.

Finally, it would be particularly desirable if a rigid cannula were available for use with the electrode, where the rigid cannula were not susceptible to capacitive coupling, but which cannula was capable of withstanding autoclave sterilization so as to be reusable.

DESCRIPTION OF THE BACKGROUND ART

The Wiltek electrosurgical probes are illustrated in a data sheet (© Wiltek Medical, Inc., 1991), which identifies particular probe models under catalog nos. LEP-37010, 37020, 37030, and 37040. The Ximed electrosurgical probes are illustrated at page 6 of catalog Ximed Surgical Accessories Price List (P/NX1290 Rev. 1). U.S. Pat. No. 4,919,129, describes an electrocautery probe having a reciprocatable electrode. French Patent Application 2,265,344, describes an electrosurgical instrument having a hook electrode at its distal tip.

U.S. Pat. No. 2,448,741 describes a complex bipolar surgical instrument having a rotating wheel and a separate translating trigger for manipulation of a needle electrode. U.S. Pat. No. 1,952,617 describes a surgical resection device having a needle electrode. E.P.O. Application No. 86300490.9 describes a tunneling angioplasty catheter. U.S. Pat. No. 4,445,892 describes a dual balloon catheter having sliding O-ring seals. U.S. Pat. Nos. 3,799,168, 3,805,791, and 4,485,812 are also generally relevant.

SUMMARY OF THE INVENTION

The present invention comprises an electrode assembly which is intended to be combined with a separate cannula for use in surgical procedures, particularly "minimally invasive surgical" procedures where the combination of electrode assembly and cannula is introduced through a trocar sleeve to a treatment site. The electrode assembly has a novel design which permits mounting in a conventional cannula having an open distal end, a proximal housing, and a central lumen extending between the open end and the housing. Usually, the cannula will include at least two valves on the proximal housing to permit separate connections for aspiration and irrigation. Separate irrigation and aspiration channels may also be used. In this way, the present invention can further provide an electrosurgical system which permits the interchange of different electrode assemblies within a single cannula. The present invention further permits the selective application of aspiration or irrigation without the need to reconnect the associated tubing. Additionally, the design of the electrode assembly of the present invention permits both rotation and axial retraction of the electrode relative to the cannula, while still providing for complete interchangeability of electrode assemblies. Finally, the present invention provides a non-conductive cannula which avoids capacitive coupling with the shaft of the electrode. Thus the present electrosurgical system eliminates the clinical danger of the cannula inadvertently discharging an induced current into a tissue or organ.

The electrode assembly comprises a shaft having a proximal end and a distal end, and a sleeve member which includes means for detachably securing the assembly to the proximal housing on the cannula. The shaft of the electrode assembly is slidably and rotatably received in an axial passage through the sleeve, thus permitting both axial and rotational positioning of the assembly relative to the cannula (when the assembly is attached to the cannula). Preferably, the axial passage includes detent stops in the retracted and extended positions, thus avoiding inadvertent extension of the electrode during irrigation, or inadvertent retraction during dissection. The electrode assembly further includes an electrode tip at the distal end of the shaft and a connector plug at the proximal end of the shaft. A sliding seal is provided within the sleeve member to inhibit fluid leakage through the sleeve when the electrode assembly is in use.

In another aspect of the present invention, a non-conductive cannula is provided for use with an electrode. Preferably, the cannula comprises a tube formed of a composite material including fiberglass in a thermoplastic resin. Ideally, the tube includes woven fiberglass tubing and a hub made from polyetherimide or an acetal. Such materials are immune from capacitive coupling, and also provide a rigid structure which is capable of withstanding repeated autoclave steam sterilization cycles. A non-conductive housing is preferably removably attached at the proximal end of the cannula, protecting the surgeon from any capacitive coupling induced discharge. Ideally, the housing includes dual trumpet valves for connection to aspiration and ventilation sources. Particularly advantageous valves for use with the present cannula are disclosed in U.S. Pat. No. 5,364,070, the disclosure of which is herein incorporated by reference. Suitable non-conductive materials for the trumpet value include polyetherimide, PEEK, and poly fenal sulfone.

The present invention further provides an electrosurgical method where the electrode assembly is introduced to a treatment site in combination with an aspiration/irrigation cannula. The electrode tip of the electrode assembly can be axially retracted and rotated relative to the cannula so that it is properly placed at the treatment site. Electrical current is then passed through the electrode tip to effect the desired severing or cauterization procedure. Optionally, the method further provides for aspirating and/or irrigating through the cannula while the electrode assembly remains in place. The method still further provides for removing the first electrode assembly and introducing a second electrode assembly to the treatment site while the cannula remains in place. When the electrode is retracted, the cannula can be used for tissue manipulation, blunt dissection, irrigation, and aspiration of fluids and smoke.

In a further aspect, the present method comprises introducing an electrode assembly to a treatment site of a grounded patient body, the electrode being disposed in a lumen of a cannula. Current is passed through the electrode within the cannula, but capacitive coupling is avoided by use of a rigid, non-conductive cannula. Preferably, the cannula comprises a high temperature material, allowing the used cannula to be steam sterilized and reused.

DESCRIPTION OF THE PREFERRED EMBODIMENTS

The present invention provides an electrode assembly and electrosurgical system useful for performing a variety of electrosurgical procedures, including both tissue dissection and tissue cauterization, where the dissected tissue will usually be subject to simultaneous cauterization. The present invention is useful for cauterizing small blood vessels in highly vascularized tissue which has been severed or otherwise damaged through use of other surgical devices.

The electrode assembly and electrosurgical system are particularly intended for use in minimally invasive surgical (MIS) procedures where the electrosurgical system (including both the electrode assembly and an attached but separable cannula as described in more detail hereinbelow) is introduced to a treatment site through a small diameter percutaneous puncture, typically through a trocar sleeve having a lumen diameter of about five millimeters or less. Such MIS procedures include laparoscopic surgery, arthroscopic surgery, and the like, where the treatment site is viewed directly or through video imaging equipment.

The electrosurgical system of the present invention comprises the novel electrode assembly in combination with an aspiration/irrigation cannula, where the cannula will optionally have a conventional design. The electrode assembly includes an elongated shaft having an electrode tip at its distal end and a connector plug at its proximal end. The shaft will usually be rigid, more usually being composed of an electrically conductive metal such as stainless steel to provide a current path between the conductor plug and the electrode tip. When composed of an electrically conductive metal, the shaft will usually be covered with an insulating material, such as tetrafluoroethylene (TFE), fluorinated ethylenepropylene (FEP), Kynar™, or another shrink wrapped plastic, over its length between the electrode tip and the connector plug. Alternatively, the shaft could be composed of a non-conductive material with a wire or other conductor electrically coupling the electrode tip with the connector plug.

The electrode assembly further includes a sleeve member secured at or near the proximal end of the shaft. The sleeve member includes an axial passage and means at one end of the passage for mounting on a proximal housing of the cannula, as described in more detail below. The proximal end of the shaft is rotatably and slidably received within the axial passage of the sleeve so that the shaft can be freely moved relative to the sleeve.

The electrode assembly further includes a means for providing a sliding seal between the shaft and the axial passage within the sleeve member, typically an O-ring mounted on the shaft or the sleeve, more typically being mounted on the shaft. Other sliding seals, such as packings, rings, and the like, would also be suitable, although not necessarily being preferred. Advantageously, the sleeve may optionally incorporate simple detent stops to retain the electrode in an extended and/or retracted position.

Alternatively, the present electrosurgical system will include a non-conductive rigid cannula. The present cannula comprises a tubular member and a housing. At least a distal portion of the tubular member is formed of a non-conductive material, to avoid capacitive coupling with a monopole electrode from discharging within a patient body. Preferably, the cannula is formed substantially entirely of non-conductive material to eliminate all danger of electrical discharge to the patient and surgeon. In a further aspect, the present tubular member is preferably formed from a high temperature material, and is removable from the housing to allow steam sterilization and facilitate cleaning, respectively. Suitable materials include composites having fiberglass in a thermoplastic resin, providing a rigid, durable structure. Such a non-conductive cannula is particularly advantageous when used with the present removable electrode assembly, as it provides an added precaution against injury caused by insulation damaged during electrode replacement.

Figure 1:
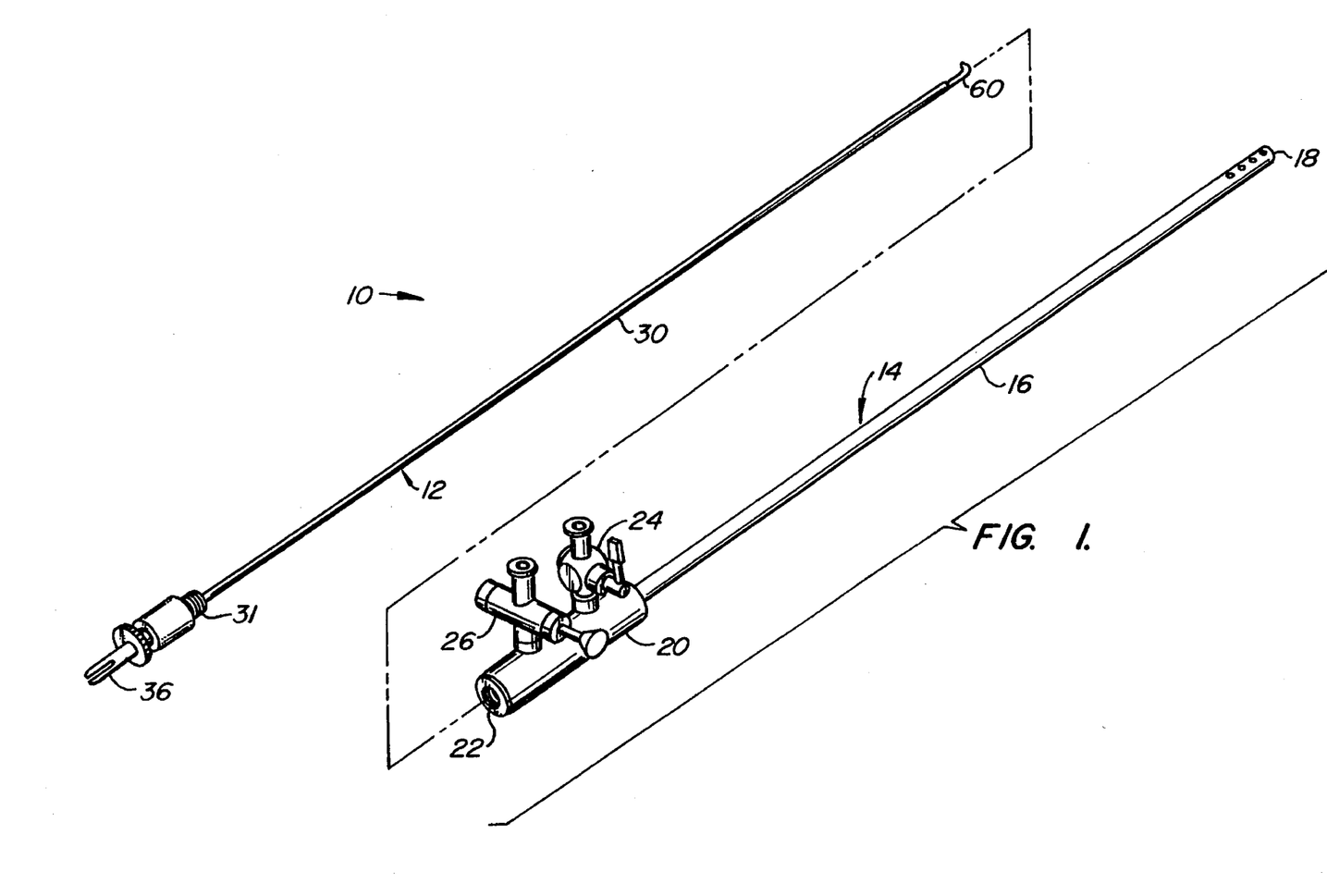
FIG. 1 is a perspective view of the electrosurgical system of the present invention including both an electrode assembly and an aspiration/irrigation cannula.
Figure 2:
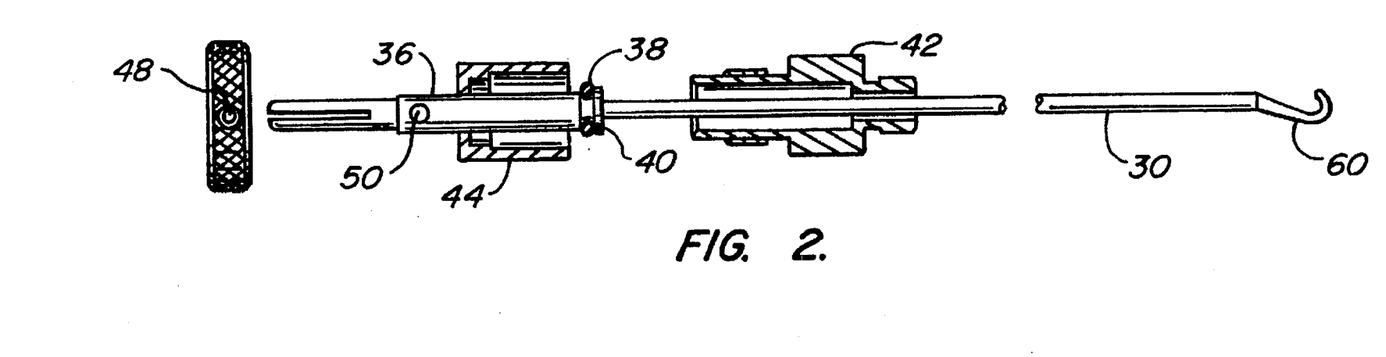
FIG. 2 is a cross-sectional view of the electrode assembly of FIG. 1, shown partially disassembled.

Referring now to FIG. 1, an electrosurgical system 10 according to the present invention includes an electrode assembly 12 and an aspiration/irrigation cannula 14. The aspiration/irrigation cannula includes a hollow tube 16 having an open distal end 18 and a proximal housing 20. The proximal housing 20 includes a proximal opening 22 which is threaded or which includes other mounting means such as a luer fitting, or the like. Proximal housing 20 further includes a pair of connection ports 24 and 26. Each connection port 24 and 26 will include an on/off valve to permit connection of an aspiration source, (i.e., a vacuum) and irrigation or perfusion source, or the like. As illustrated, connection port 24 comprises, a stopcock and connection port 26 comprises a trumpet valve. It would, of course, be possible to utilize two stopcocks, two trumpet valves, or any other conventional on/off valve for connecting the aspiration and irrigation sources.

Referring now to FIGS. 1–4, the electrode assembly 12 comprises shaft 30, which may be a substantially solid metal rod coated with an insulating material, such as Teflon®. A sleeve member 32 includes an axial passage 34 which slidably receives the proximal end of the shaft 30. A plug connector 36 is connected to the distal end of the rod 30 and carries an O-ring 38 in an O-ring holder 40. The sleeve 32 includes a distal half 42 and a proximal half 44, where the halves 42 and 44 may be brought together to secure the O-ring 38 in O-ring holder 40 within the axial passage 34. In this way, the O-ring 38 provides for a sliding seal within the sleeve member 32.

Figure 3:
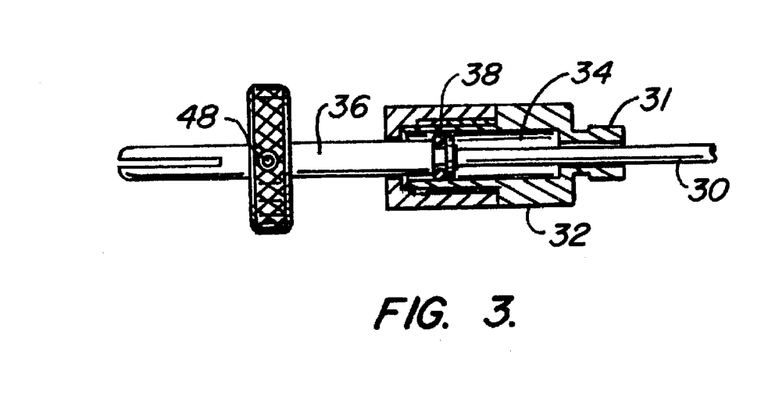
FIG. 3 is a detailed view of the proximal end of the electrode assembly of FIGS. 1 and 2, shown with the shaft in a generally retracted configuration.
Figure 4:
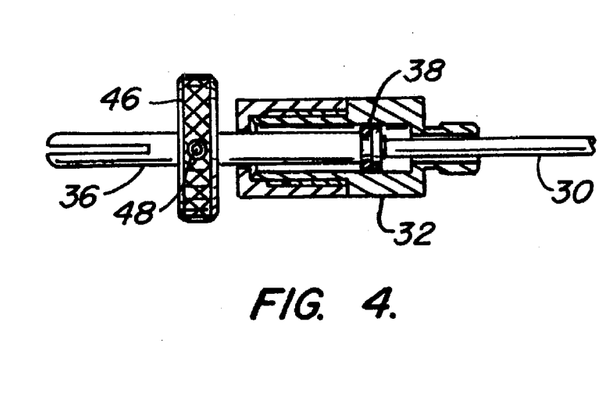
FIG. 4 is a view similar to FIG. 3, shown with the shaft in a generally extended configuration.

As illustrated in FIG. 3, the rod 30 and plug 36 may be translated in the proximal direction relative to the sleeve 32. As illustrated in FIG. 4, the rod may also be translated in the distal direction relative to the sleeve 32. To facilitate manual translation and rotation of the rod 30, a thumb wheel 46 is mounted on the connector plug 36. Conveniently, the thumb wheel may be held in place by a set screw 48 which is received in retaining hole 50 on the plug connector 36.

Figure 5A:
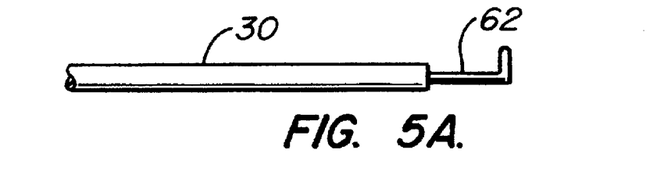
FIGS. 5A and 5B illustrate a bent wire electrode tip which could be used in place of the hook electrode on the electrode assembly of FIGS. 1–4.
Figure 5B:
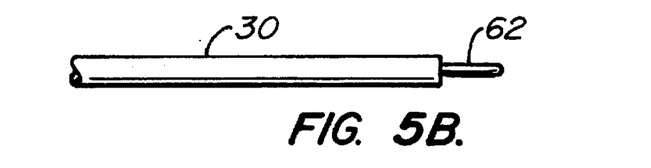
Figure 6A:
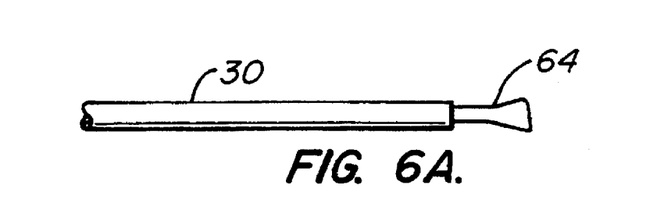
FIGS. 6A and 6B illustrate a spatula electrode tip which could be used in place of the hook electrode on the electrode assembly of FIGS. 1–4.
Figure 6B:
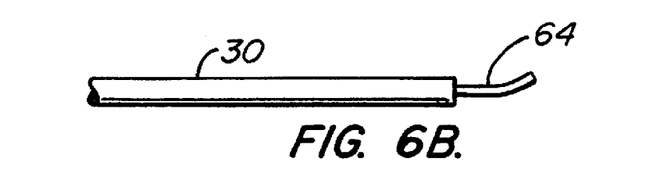
Figure 7:
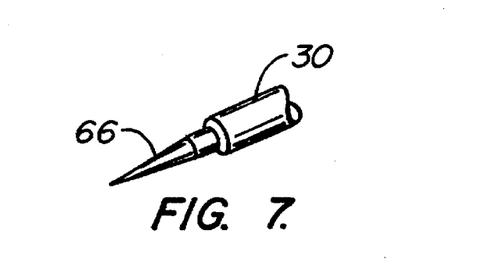
FIG. 7 is a perspective view of a needle electrode tip which could be used in place of the hook electrode on the electrode assembly of FIGS. 1–4.
Figure 8:
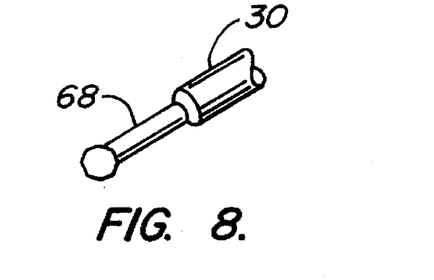
FIG. 8 is a perspective view of a ball electrode tip which could be used in place of the hook electrode on the electrode assembly of FIGS. 1–4.

As illustrated in FIGS. 1–4, a hook electrode 60 is disposed on the proximal end of the shaft 30. A variety of other electrode configurations can also be employed. As illustrated in FIGS. 5A and 5B, a bent wire electrode tip 62 may be secured to the distal end of shaft 30. The remainder of the electrode assembly 12 can be unchanged. A spatula electrode design 64 is illustrated in FIGS. 6A and 6B. Similarly, a needle electrode 66 as seen in FIG. 7, or a ball electrode 68 as seen in FIG. 8 may be used in place of hook electrode 60 of FIGS. 1-4.

Figure 9:
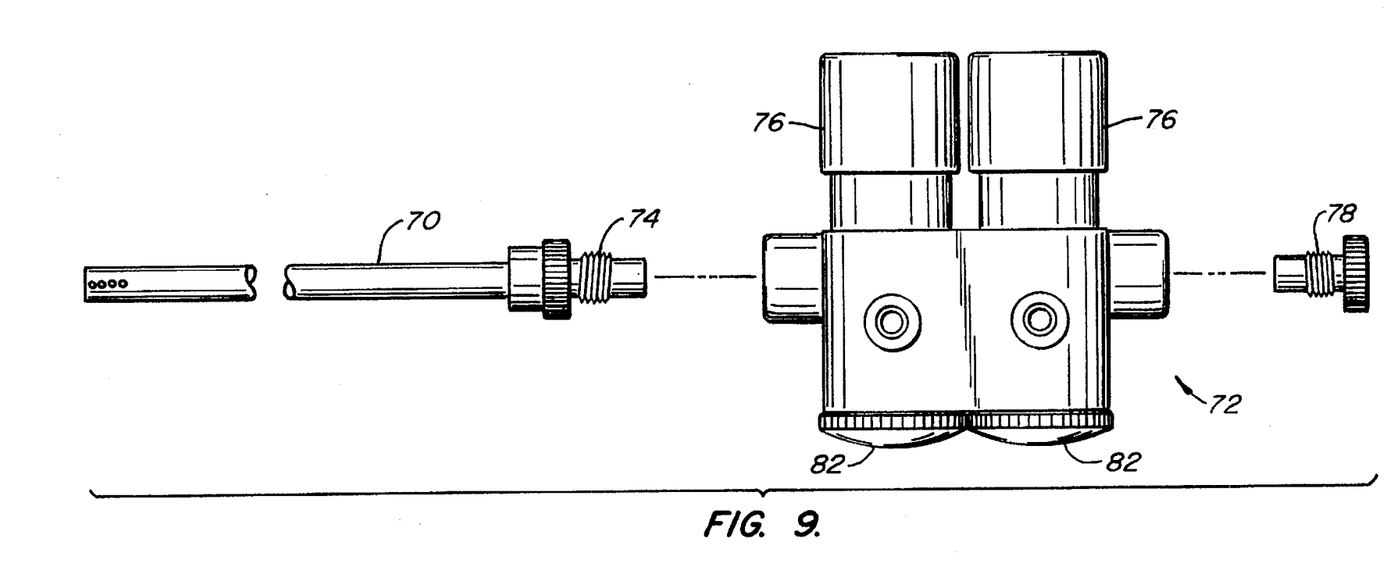
FIG. 9 illustrates an exemplary cannula according to the present invention.

As illustrated in FIG. 9, an exemplary cannula according to the present invention comprises a non-conductive tubular member 70 and a non-conductive proximal housing 72. Non-conductive tubular member 70 is formed of a rigid, high temperature composite material, such as woven fiberglass in a thermoplastic resin. The exemplary embodiment shown measures roughly 5 mm in diameter and 33 cm in length. A proximal threaded hub 74 allows removal of non-conductive housing 72 to facilitate cleaning. Advantageously, threaded hub 74 may be formed of polyetherimide or an acetal, and may be bonded with epoxy to the woven fiberglass tube.

Non-conductive housing 72 includes two trumpet valves 76 for connection to an aspiration source and an irrigation source. Exemplary valves for use with the present non-conducting housing are disclosed in U.S. Pat. No. 5,364,070, previously incorporated by reference. Proximal housing is preferably formed of a non-conductive material such as polyetherimide, PEEK, or poly fenal sulfone, thereby avoiding any capacitive coupling and allowing autoclave sterilization of both subassemblies of the present cannula. Finally, a sealing end cap 78 is provided for sealing the electrode assembly port of the proximal housing when no electrode is installed.

Figure 10:
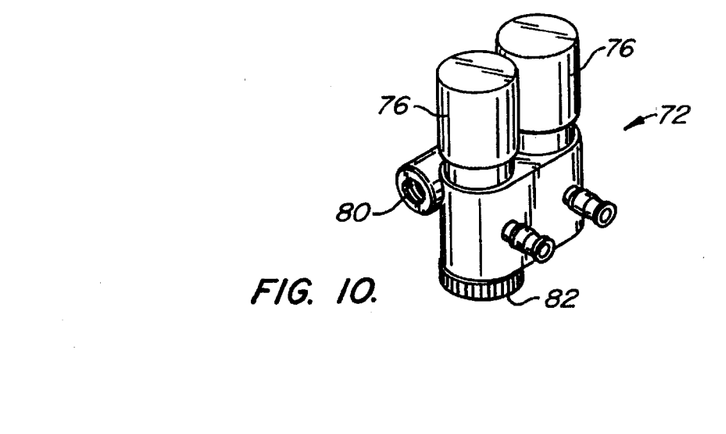
FIG. 10 is a perspective view of a proximal housing of the exemplary cannula of FIG. 9.

Referring now to FIG. 10, a perspective view of non-conductive proximal housing 72 is shown. Threads 80 for connection to threaded hub 74 of non-conductive tubular member 70 are clearly visible. Advantageously, valves 76 are accessible through bottom caps 82 for cleaning and sterilization.

Figure 11:
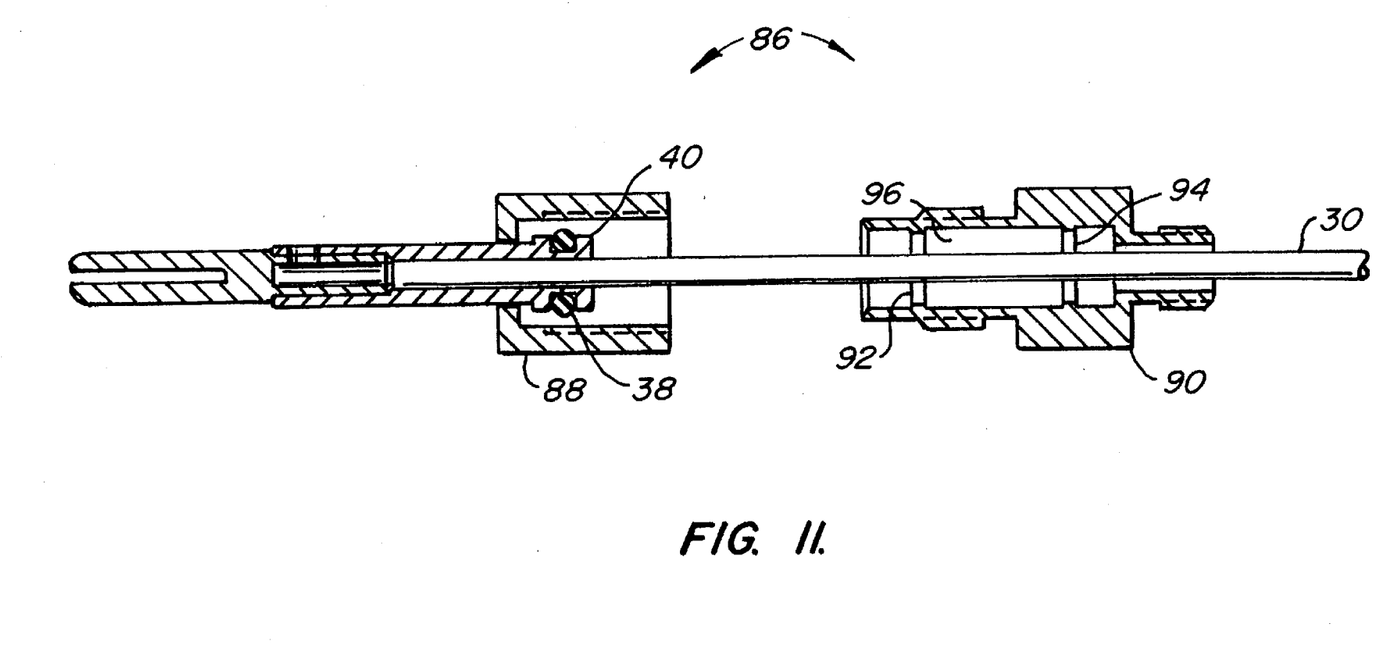
FIG. 11 is a cross-sectional view of an embodiment of an electrode sleeve having detent stops for the extended and the retracted positions, shown partially disassembled.

FIG. 11 illustrates an embodiment of the present electrode assembly having detent stops in both the extended and retracted positions. As described above, shaft 30 carries O-ring 38 in O-ring holder 40. A detent sleeve 86 again includes a proximal half 88 and a distal half 90. In this embodiment, distal half 90 further includes a retracted detent 92 and an extended detent 94 which protrude into axial passage 96. When proximal half 88 and distal half 90 are joined, O-ring 38 rides within axial passage 96. O-ring 38 must be compressed to pass retracted detent 92 or extended detent 94, thereby preventing inadvertent axial movement of the electrode relative to the sleeve and cannula when the electrode is fully extended or retracted. Advantageously, the retracted electrode will not be extended by application of high pressure irrigation, while the extended electrode will not be retracted when the surgeon applies pressure to the electrode tip during dissection.

In use, a first electrode assembly, e.g., having a hook electrode tip 60, will be inserted into the aspiration/irrigation cannula 14, with threaded connector 31 being received in threaded connector 22 of the proximal housing 20. After the aspiration/irrigation cannula is generally in place, the electrode tip 60 can be axially and rotationally positioned to precisely the desired location. Current can then be applied through a conventional power supply which is connected to the connector plug 36. Such power supplies are available from commercial suppliers, such as Valleylab, Inc., (a Pfizer Company), Boulder, Colo.; Aspen Labs., Inc., (a Conmed Company), Englewood, Colo.; Birtcher Corp., Irvine, Calif.; and Bard Electro Medical Systems, Inc., Englewood, Colo.

Its particular advantage of the electrosurgical system 10 of the present invention is that after an electrosurgical procedure has been completed, smoke and fluids in the treatment area can be aspirated by opening one of the connection ports 24 or 26 connected to an aspiration source. Additionally, the area can be irrigated with a desired irrigation fluid by opening the other of the connection ports 24 and 26 connected to an irrigation source. It is particularly convenient that two connection ports are provided so that both aspiration and irrigation can be alternated (or performed simultaneously) and repeated without the need to reconnect either the aspiration or irrigation source.

The electrosurgical system of the present invention further allows for removal of the first electrode assembly and replacement with a second electrode assembly without removal of the aspiration/irrigation cannula 14 from the treatment site. In particular, if electrode assembly 30 is removed by unscrewing the sleeve 32 from the proximal housing 20 on the cannula 14. The second electrode assembly, typically having a different electrode tip configuration, can then be introduced without the need to remove the cannula 14. Of course, the second electrode assembly can also be axially retracted and rotationally adjusted relative to the cannula after its sleeve has been secured to the cannula housing 20.

Although the foregoing invention has been described in detail for purposes of clarity of understanding, it will be obvious that certain modifications may be practiced within the scope of the appended claims.

What is claimed is:

1. An electrode assembly for use in combination with a cannula having an open distal end, a proximal housing, and a lumen extending from the open distal end through the housing, said electrode assembly comprising:

a sleeve having an axial passage from a distal end to a proximal end, a distal half with a distal limit, a proximal half with a proximal limit which is proximal of the distal limit, and a means for detachably securing the sleeve to the proximal housing of the cannula;

a shaft translatably and rotatably disposed within the axial passage, the shaft having a proximal end, a distal end, and a holder structure attached distally of the proximal end, the holder being disposable between the distal limit and the proximal limit;

an electrode tip disposed at the distal end of the shaft;

a connector plug disposed at the proximal end of the shaft and electrically coupled to the electrode tip; and a thumb wheel disposed on the shaft proximal of the sleeve, wherein the thumb wheel precisely rotationally and axially positions the electrode relative to the sleeve while the sleeve contains the holder between the proximal limit and the distal limit.

2. An electrode assembly for use in combination with a cannula having an open distal end, a proximal housing, and a lumen extending from the housing to the open distal end, said electrode assembly comprising:

a rigid shaft having a proximal end, a distal end, and a holder structure distal of the proximal end;

a sleeve member comprising an enclosure defining two spaced apart walls, an axial passage through said enclosure, and means at one end of the passage for detachably securing the sleeve member to the proximal housing of the cannula, wherein the shaft is slidably and rotatably received in the axial passage of the sleeve member while said detachable securing means are secured, and wherein said spaced apart walls axially contain the holder within the enclosure;

means within the sleeve member for providing a sliding seal with the shaft to inhibit fluid leakage through the sleeve;

an electrode tip disposed at the distal end of the shaft;

a connector plug disposed at the proximal end of the shaft and electrically coupled to the electrode tip; and a thumb wheel secured to the shaft proximal of the holder, wherein axial translation and rotation of the thumb wheel axially and rotationally positions the electrode relative to the sleeve member.

3. An electrode assembly as in claim 2, wherein the shaft is formed from an electrically conductive material to electrically couple the connector plug to the electrode tip.

4. An electrode assembly as in claim 2, wherein the sleeve member defines a cylindrical enclosure having a threaded connector at one end and wherein the sliding seal means comprises an O-ring mounted on the shaft which slides within the cylindrical enclosure.

5. An electrode assembly as in claim 2, wherein the electrode tip has a configuration selected from the group consisting of hook, spatula, bent wire, needle, and ball.

6. An electrode assembly as claimed in claim 2, wherein a retracted detent protrudes into the axial passage such that the electrode tip is releasably restrained in a retracted axial position when the sliding sealing means is proximal of the retracted detent.

7. An electrode assembly as claimed in claim 2, wherein an extended detent protrudes into the axial passage such that the electrode tip is releasably restrained in an extended axial position when the sliding sealing means is distal of the extended detent.

8. An electrosurgical instrument system comprising:

a cannula, wherein the cannula comprises a tubular member having an open distal end, a proximal housing opposite the open distal end, and a lumen extending from the housing to the open distal end, wherein at least two valves are mounted on the proximal housing for connection to a perfusion source and an aspiration source; and a plurality of interchangeable electrode assemblies, wherein each electrode assembly comprises:

a rigid shaft having a proximal end, a distal end, and a holder structure distal of the proximal end;

a sleeve member comprising an enclosure defining two spaced apart walls, an axial passage through said enclosure, and means at one end of the passage for detachably securing the sleeve member to the proximal housing of the cannula, wherein the shaft is slidably and rotatably received in the axial passage of the sleeve member and the shaft extends into the lumen while said sleeve member remains secured to the cannula, and wherein said spaced apart walls axially contain the holder within the enclosure;

means within the sleeve member for providing a sliding seal with the shaft to inhibit fluid leakage through the sleeve;

a single thumb wheel secured to the shaft proximal of the holder, wherein axial translation and rotation of the thumb wheel shaft axially and rotationally positions the electrode relative to the sleeve member;

an electrode tip disposed at the distal end of the shaft; and a connector plug disposed at the proximal end of the shaft and electrically coupled to the electrode tip;

wherein at least two of the electrode assemblies differ by having electrode tips of differing configuration.

9. An electrosurgical system as in claim 8, wherein the shaft is formed from an electrically conductive material to electrically couple the connector plug to the electrode tip.

10. An electrosurgical system as in claim 8, wherein the sleeve member is a cylindrical enclosure having a threaded connector at one end and wherein the sliding seal means is an O-ring mounted on the shaft which slides within the cylindrical enclosure.

11. An electrosurgical system as in claim 8, wherein the electrode tip has a configuration selected from the group consisting of hook, spatula, bent wire, needle, and ball.

12. An electrosurgical system as claimed in claim 8, wherein the tubular member comprises a non-conductive material such that capacitive coupling with the shaft of the electrode is avoided.

13. An electrosurgical system as claimed in claim 12, wherein the non-conductive material is capable of withstanding repeated steam sterilization cycles.

14. An electrosurgical system as claimed in claim 13, wherein the non-conductive material comprises fiberglass in a thermoplastic resin.

15. An electrosurgical system as claimed in claim 10, wherein a detent extends into the cylindrical enclosure so as to releasably restrain axial translation of the electrode by compression of the O-ring.

16. An electrosurgical assembly comprising:

at least one interchangeable electrode assembly including:

a sleeve having an axial passage from a distal end to a proximal end, a distal limit, a proximal limit, an extended detent, a retracted detent and a means for detachably securing the sleeve to the cannula, a shaft translatably and rotatably disposed within the axial passage, the shaft having a holder structure between the distal limit and the proximal limit, an O-ring which slidably seals between the holder and the axial passageway, an electrode tip disposed at the distal end of the shaft, and a thumb wheel disposed on the shaft proximal of the sleeve, wherein the thumb wheel rotationally and axially positions the electrode relative to the sleeve while the sleeve contains the holder between the proximal limit and the distal limit, and wherein the O-ring releasably restrains the electrode in a retracted position when proximal of the retracted detent, and in an extended position when distal of the extended detent; and a cannula including;

a rigid tubular body having an open distal end, a proximal end, and a lumen therebetween, and a housing disposed at the proximal end of the tubular body, the housing including two trumpet valves for connection to an aspiration source and an irrigation source, wherein the tubular body comprises woven fiberglass in a thermoplastic resin to eliminate capacitive coupling, and wherein the housing comprises a non-conductive material selected from the group containing polyethermide, PEEK, and poly fenal sulfone.

17. An electrosurgical method comprising:

introducing a first electrode assembly to a treatment site in combination with a aspiration/irrigation cannula, said first electrode assembly having a sleeve member at a proximal end of the electrode assembly;

detachably securing the sleeve member of the first electrode assembly to a proximal end of the cannula;

axially and rotationally positioning a shaft of the first electrode assembly relative to both the sleeve member and the cannula by manipulating a single thumb wheel relative to the sleeve to position an electrode tip on the first electrode assembly against tissue, wherein proximal and distal movement of the electrode tip relative to the cannula is limited while said first electrode assembly remains secured to the cannula;

passing current through the electrode tip to effect severing or cauterization of the tissue at the treatment site;

detaching the sleeve member of the first electrode assembly from the cannula while the cannula remains in place;

removing the first electrode assembly from the cannula; and introducing a second electrode assembly to the treatment site while the cannula remains in place, and detachably securing a sleeve member of the second electrode assembly to the proximal end of the cannula.

18. An electrosurgical method as in claim 17, further comprising aspirating the treatment site by applying a vacuum to the proximal end of the cannula while the electrode assembly remains in place.

19. An electrosurgical method as in claim 17, further comprising irrigating the treatment site by introducing an irrigation fluid through the proximal end of the cannula while the electrode assembly remains in place.

20. An electrosurgical method as claimed in claim 17, further comprising avoiding capacitive coupling of the cannula with the first and second electrode assemblies, the tubular member being composed of a non-conductive material.

21. An electrosurgical method as claimed in claim 20, further comprising:

removing the cannula; and sterilizing the tubular member in an autoclave.

* * * * *